US 10,684,279 B2

(12) United States Patent
Kanai et al.

(10) Patent No.: US 10,684,279 B2
(45) Date of Patent: Jun. 16, 2020

(54) DEVICE FOR OPERATING MAGNETIC PARTICLES

(71) Applicant: SHIMADZU CORPORATION, Kyoto-shi, Kyoto (JP)

(72) Inventors: Masaki Kanai, Kyoto (JP); Hiroyuki Jikuya, Kyoto (JP); Tetsuo Ohashi, Kyoto (JP); Seiya Fujiwara, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 198 days.

(21) Appl. No.: 15/891,509

(22) Filed: Feb. 8, 2018

(65) Prior Publication Data

US 2018/0224442 A1    Aug. 9, 2018

(30) Foreign Application Priority Data

Feb. 9, 2017  (JP) ................. 2017-021912

(51) Int. Cl.
| | | |
|---|---|---|
| *G01N 33/543* | (2006.01) | |
| *G01N 1/34* | (2006.01) | |
| *B03C 1/00* | (2006.01) | |
| *G01N 1/40* | (2006.01) | |

(52) U.S. Cl.
CPC ......... *G01N 33/54326* (2013.01); *G01N 1/34* (2013.01); *B03C 2201/18* (2013.01); *B03C 2201/26* (2013.01); *G01N 2001/4083* (2013.01)

(58) Field of Classification Search
None
See application file for complete search history.

(56) References Cited

U.S. PATENT DOCUMENTS

| | | | | |
|---|---|---|---|---|
| 2013/0273552 | A1* | 10/2013 | Ohashi .................. | B01L 3/5025 435/6.12 |
| 2016/0209393 | A1* | 7/2016 | Dimson ............... | G01N 33/487 |

FOREIGN PATENT DOCUMENTS

WO    2012/086243 A1    6/2012

* cited by examiner

*Primary Examiner* — Ryan B Huang
(74) *Attorney, Agent, or Firm* — Sughrue Mion, PLLC

(57) ABSTRACT

To provide a device for operating magnetic particles capable of treating large quantity, and retaining a gel-like medium layer stably, a vessel is formed so that an area perpendicular to a longitudinal direction in a large-diameter part packed with a liquid layer is larger than an area perpendicular to the longitudinal direction in the small-diameter part packed with a gel-like medium layer. Therefore, in the vessel, it is possible to reduce the diameter of the small-diameter part while keeping the capacity of the large-diameter part large. As a result, in the vessel, it is possible to treat large quantity in the liquid layer, and it is possible to retain the gel-like medium layer stably.

6 Claims, 7 Drawing Sheets

DEVICE FOR OPERATING MAGNETIC PARTICLES

BACKGROUND OF THE INVENTION

Field of the Invention

The present invention relates to a device for operating magnetic particles, including a tubular vessel formed with an internal space where a gel-like medium layer and a liquid layer are alternately stacked in a longitudinal direction, and magnetic particles are packed.

Description of the Related Art

In medical examinations, food safety and hygiene management, monitoring for environmental protection and the like, it is demanded to extract a target substance from a sample containing a variety of impurities and to subject the target substance to detection or reaction. For example, in medical examinations, it is required to detect, identify and quantify nucleic acid, protein, sugar, lipid, bacteria, viruses, radioactive substances and the like contained in blood, serum, cells, urine, feces and the like separated and obtained from animals or vegetables. In these examinations, it is sometimes required to separate and purify a target substance so as to eliminate an adverse effect of background or the like caused by impurities.

In order to separate and purify a target substance in a sample, a method of using magnetic particles having a chemical affinity with the target substance or a molecular recognizing function on the surface of magnetic bodies with a particle diameter of about 0.5 μm to ten-odd μm has been developed and brought into practice. In the method, after fixing a target substance to the surface of the magnetic particles, the magnetic particles are separated and collected from a liquid phase by operating the magnetic field, and as necessary, the collected magnetic particles are dispersed in a liquid phase of a washing liquid or the like, and the step of separating and collecting the magnetic particles from the liquid phase is repeated. Thereafter, by dispersing the magnetic particles in an eluent, the target substance fixed to the magnetic particles is released in the eluent and the target substance in the eluent is collected. Use of the magnetic particles enables collection of the target substance by magnet, and thus is advantageous in automatization of chemical extraction and purification.

As such a method for separating and purifying a target substance, a method of using a tubular vessel such as a capillary has been proposed (for example, see WO 2012/086243).

In the method disclosed in WO 2012/086243, a liquid layer of a lysis/binding liquid, a washing liquid, an eluent or the like, and a gel-like medium layer are stacked alternately in a tubular vessel (tubular device) such as a capillary. Then, after introducing magnetic particles and a sample into the tubular device, a magnetic field applying means such as a permanent magnet is brought close to the tubular device. Thereafter, by moving the magnetic field applying means along the longitudinal direction of the tubular device, magnetic particles are migrated following the magnetic field applying means, and thus the target substance is separated and purified.

In the case of separating and purifying a target substance in a sample as described above, the capability of treating a large amount of sample in one operation is desired. For example, in the conventional tubular device as described above, by increasing the inner diameter, it is possible to increase the amount of sample that is introduced into the tube, and it is possible to treat a large amount of sample in one operation. Here, in the tubular device, the gel-like medium layer is retained at a certain position in the tube by its own viscosity. As the diameter of the tube increases, the weight of gel-like medium layer per unit area of the tube increases. As a result, the gel-like medium layer cannot be retained in the tube stably, and the trouble of flowing of the gel-like medium layer due to oscillation during transportation, and the trouble of mixing of the liquid layers that are separated by the gel-like medium layer occur.

The present invention was devised in light of the aforementioned circumstances, and it is an object of the present invention to provide a device for operating magnetic particles capable of treating large quantity, and retaining a gel-like medium layer stably.

SUMMARY OF THE INVENTION (1) A device for operating magnetic particles according to the present invention includes a tubular vessel formed with an internal space where a gel-like medium layer and a liquid layer are alternately stacked in a longitudinal direction and magnetic particles are packed. In the device for operating magnetic particles, an area of a first cross section that is perpendicular to the longitudinal direction in a part packed with the liquid layer in the internal space of the vessel is larger than an area of a second cross section that is perpendicular to the longitudinal direction in a part packed with the gel-like medium layer.

According to such a configuration, in the tubular vessel, it is possible to reduce the diameter of the part packed with the gel-like medium layer while keeping the capacity of the part packed with the liquid layer large.

Therefore, in the tubular vessel, it is possible to treat large quantity in the liquid layer, and it is possible to retain the gel-like medium layer stably.

(2) In the vessel, a sample introduction space, and a sample migration space may be formed. In the sample introduction space, a sample is introduced. In the sample migration space, a gel-like medium layer and a liquid layer are alternately stacked in the longitudinal direction, and a target component contained in the sample in the sample introduction space is migrated in the longitudinal direction while it is fixed to the magnetic particles. The first cross section may be a section perpendicular to the longitudinal direction in a part packed with the liquid layer in the sample migration space. The second cross section may be a section perpendicular to the longitudinal direction in a part packed with the gel-like medium layer in the sample migration space.

According to such a configuration, in a part of the vessel where a sample migration space which is a space for migrating a target component contained in a sample while it is fixed to the magnetic particles is formed, it is possible to reduce the diameter of the part packed with the gel-like medium layer while keeping the capacity of the part packed with the liquid layer large.

(3) The vessel may be formed with an opposing surface where a magnetic field application part is opposed and moved in the longitudinal direction. The first cross section may have an inner diameter in a direction parallel with the opposing surface larger than an inner diameter in a direction perpendicular to the opposing surface.

According to such a configuration, in the case where the magnetic field application part is opposed to the opposing surface of the vessel, it is possible to keep the dimension between the magnetic field application part and the magnetic particles inside the vessel small.

Therefore, it is possible to securely make the magnetic force of the magnetic field application part act on the magnetic particles inside the vessel, while keeping the capacity of the part packed with the liquid layer in the vessel large.

As a result, when the magnetic field application part is moved in the longitudinal direction, it is possible to let the magnetic particles migrate inside the vessel smoothly following the magnetic field application part.

(4) The first cross section and the second cross section may be flush with each other in a part opposed to the magnetic field application part on the opposing surface side when viewed along the longitudinal direction.

According to such a configuration, when the magnetic field application part is moved in the longitudinal direction along the opposing surface of the vessel, it is possible to let the magnetic particles migrate smoothly inside the vessel.

(5) The part packed with the liquid layer and the part packed with the gel-like medium layer in the internal space of the vessel may be connected with each other by a tapered surface inclined with respect to the longitudinal direction.

According to such a configuration, when the magnetic particles migrate inside the vessel, it is possible to prevent the magnetic particles remaining at the boundary between the part packed with the liquid layer and the part packed with the gel-like medium layer.

Therefore, it is possible to let the magnetic particles migrate smoothly inside the vessel.

(6) The liquid layer may include a washing layer and an elution layer. The washing layer is packed with a washing liquid for washing a target substance in a sample. The elution layer is packed with an eluent for eluting a target component in a sample. The first cross section may be a section perpendicular to the longitudinal direction of the washing layer in the internal space of the vessel.

According to such a configuration, it is possible to keep the capacity of the part of the vessel packed with the washing layer large.

Therefore, in the tubular vessel, a large amount of the washing layer can be packed.

According to the present invention, in the tubular vessel, it is possible to reduce the diameter of the part packed with the gel-like medium layer while keeping the capacity of the part packed with the liquid layer large. Therefore, in the tubular vessel, it is possible to treat large quantity in the liquid layer, and it is possible to retain the gel-like medium layer stably.

DETAILED DESCRIPTION OF THE PREFERRED EMBODIMENTS

Figure 1:
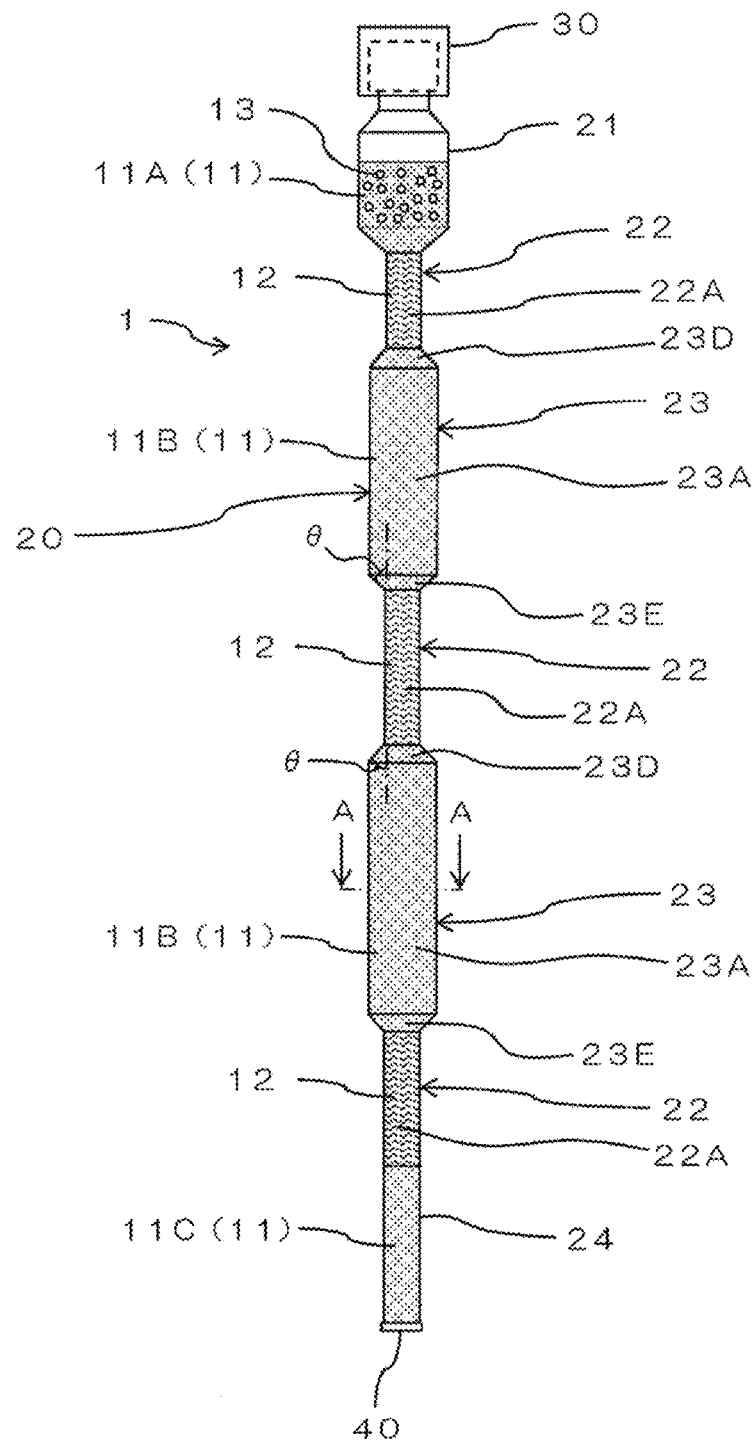
FIG. 1 is a front view showing a configuration example of a device for operating magnetic particles according to one embodiment of the present invention.
Figure 2:
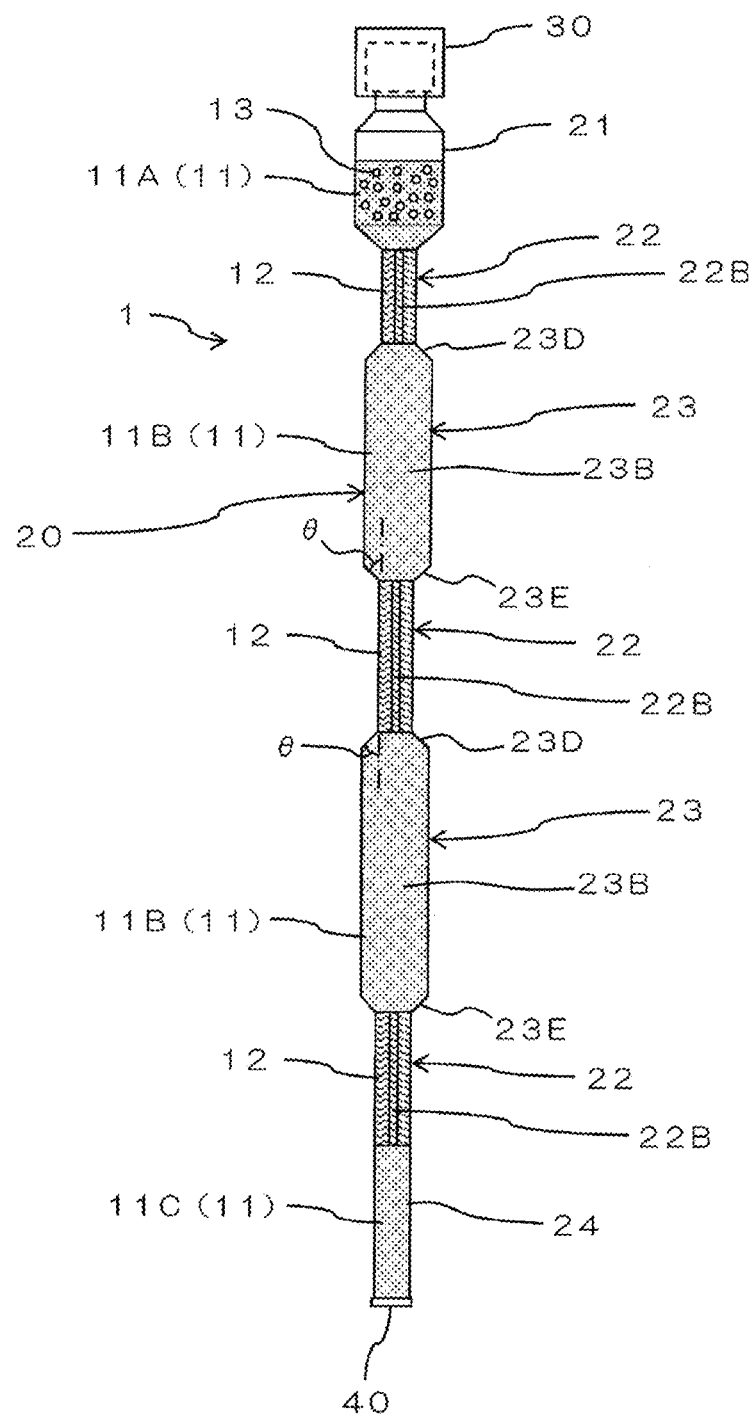
FIG. 2 is a back view showing a configuration example of the device for operating magnetic particles of FIG. 1.
Figure 3:
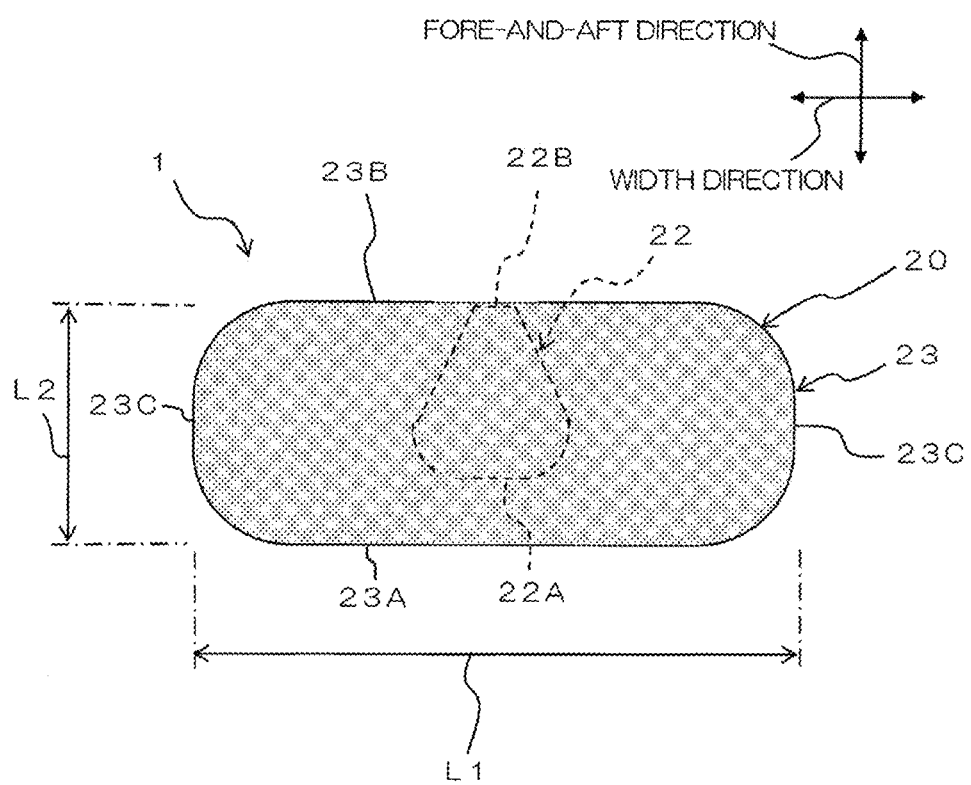
FIG. 3 is an A-A section view of the device for operating magnetic particles of FIG. 1.

1. Configuration of Device for Operating Magnetic Particles (1) Internal Configuration of Device for Operating Magnetic Particles FIG. 1 is a front view showing a configuration example of a device for operating magnetic particles 1 according to one embodiment of the present invention. FIG. 2 is a back view showing a configuration example of the device for operating magnetic particles 1 of FIG. 1. FIG. 3 is an A-A section view of the device for operating magnetic particles 1 of FIG. 1. The device for operating magnetic particles 1 (hereinafter, referred to as "device 1") is provided for extracting and purifying a target substance from a liquid sample, and includes a tubular vessel 20 extending in a straight line.

Inside the vessel 20, a plurality of liquid layers 11 and a plurality of gel-like medium layers 12 are formed. Specifically, the liquid layer 11 is formed in the lowermost part of the vessel 20, and the gel-like medium layer 12 and the liquid layer 11 are alternately stacked upwardly along the longitudinal direction. In this example, four liquid layers 11 and three gel-like medium layers 12 are alternately formed in the longitudinal direction (vertical direction); however, the number of liquid layers 11 and the number of gel-like medium layers 12 can be arbitrarily set without limited to the above.

The liquid layer 11 in the uppermost part of the vessel 20 is a liquid sample containing a target substance, and is packed with a large number of magnetic particles 13. The liquid layer 11 in the uppermost part of the vessel 20 is a fixing layer 11A for fixing the target substance to the magnetic particles 13. The liquid layer 11 in the lowermost part of the vessel 20 is an elution layer 11C for eluting the target substance in the liquid sample. One or a plurality of (two in this example) liquid layers 11 in the middle part of the vessel 20 is a washing layer 11B for removing impurities contained in the liquid sample. These liquid layers 11 are separated from each other by the gel-like medium layer 12. The target substance contained in the liquid sample is fixed to the magnetic particles 13 in the fixing layer 11A, and then subjected to an operation of moving from the uppermost part to the lowermost part of the vessel 20 by varying the magnetic field (particle operation), and washed by the washing layer 11B during the operation, and eluted in the elution layer 11C in the lowermost part.

The magnetic particles 13 are particles capable of specifically fixing a target substance such as nucleic acid or antigen on the surface or in the interior thereof. By dispersing the magnetic particles 13 in the liquid layer 11 in the uppermost part of the vessel 20 (fixing layer 11A), the target substance contained in the liquid layer 11 is selectively fixed to the magnetic particles 13.

The method for fixing the target substance to the magnetic particles 13 is not particularly limited, and various known fixing mechanisms such as physical adsorption, chemical adsorption and the like are applicable. For example, the target substance is fixed on the surface or the interior of the magnetic particles 13 by various intermolecular forces such as, for example, van der Waals force, hydrogen bond, hydrophobic interaction, interionic interaction, and π-π stacking.

The particle diameter of the magnetic particles 13 is preferably 1 mm or less, more preferably 0.1 μm to 500 μm, further preferably 3 to 5 μm. Regarding the shape of the magnetic particles 13, globular shapes with uniform particle diameters are desired; however, irregular shapes having a certain degree of particle diameter distribution may be employed as long as the particle operation is allowed. The magnetic particles 13 may be formed of a single substance, or may be formed of a plurality of components.

While the magnetic particles 13 may be formed only of magnetic bodies, magnetic bodies having a coating for specifically fixing a target substance on their surface are preferably used. Examples of the magnetic body include iron, cobalt, nickel, and compounds, oxides and alloys thereof. Concrete examples include magnetite ($Fe_3O_4$), hematite ($Fe_2O_3$ or $\alpha Fe_2O_3$), maghemite ($\gamma Fe_2O_3$), titanomagnetite ($xFe_2TiO_4.(1-x)Fe_3O_4$), ilmenohematite ($xFeTiO_3.(1-x)Fe_2O_3$), pyrrhotite ($Fe_{1-x}S(x=0$ to $0.13).Fe_7S_8$ ($x\sim0.13$)), greigite ($Fe_3S_4$), goethite ($\alpha FeOOH$), chromium oxide ($CrO_2$), permalloy, an alnico magnet, stainless, a samarium magnet, a neodymium magnet, and a barium magnet.

Examples of the target substance that is selectively fixed to the magnetic particles 13 include biological substances such as nucleic acid, protein, sugar, lipid, antibody, receptor, antigen, ligand and the like, and cells themselves. When the target substance is a biological substance, the target substance may be fixed to the interior or the surface of the magnetic particles 13 by molecular recognition or the like. For example, when the target substance is nucleic acid, magnetic particles having the silica-coated surface are preferably used as the magnetic particles 13. When the target substance is an antibody (for example, labeling antibody), a receptor, an antigen, a ligand and the like, it is possible to selectively fix the target substance on the surface of the particles via an amino group, a carboxyl group, an epoxy group, avidin, biotin, digoxigenin, protein A, protein G and the like on the surface of the magnetic particles 13. As the magnetic particles 13 capable of selectively fixing a specific target substance, for example, Dynabeads (registered trademark) available from Life Technologies, MagExtractor (registered trademark) available from TOYOBO and the like commercially available products can be used.

When the target substance is nucleic acid, the washing liquid (washing layer 11B) can be the one that releases components other than nucleic acid contained in the liquid sample (for example, protein, sugar and the like), a reagent used for treatment such as nucleic acid extraction and the like into the washing liquid while keeping the nucleic acid fixed on the surface of the magnetic particles 13. Examples of the washing liquid (washing layer 11B) include high salt concentration aqueous solutions of sodium chloride, potassium chloride, ammonium sulfate and the like, and alcohol aqueous solutions such as ethanol, and isopropanol.

As the eluent for eluting nucleic acid (elution layer 11C), water or a buffer containing a salt in low concentration can be used. Concretely, a Tris buffer, a phosphate buffer, distilled water and the like can be used, and 5 to 20 mM Tris buffer adjusted to have pH 7 to 9 is generally used. By dispersing the magnetic particles 13 to which nucleic acid is fixed in the eluent, it is possible to release and elute the nucleic acid in a nucleic acid eluate. The collected nucleic acid can be subjected to analysis, reaction or the like after undergoing operations such as concentration and drying to solid as necessary.

The gel-like medium layer 12 is gel-like or paste-like before the particle operation. The gel-like medium layer 12 is preferably formed of a substance that is insoluble or hardly soluble in the adjacent liquid layer 11 and is chemically inactive. The wording "insoluble or hardly soluble in liquid" used herein means that the solubility in the liquid at 25° C., is approximately 100 ppm or less. The wording "chemically inactive substance" used herein means a substance that does not chemically influence on the liquid layer 11, the magnetic particles 13 and the substance fixed to the magnetic particles 13 by contact with the liquid layer 11, or the operation of the magnetic particles 13 (the operation of making the magnetic particles 13 migrate in the gel-like medium layer 12).

The material and composition of the gel-like medium layer 12 are not particularly limited, and physical gel or chemical gel may be used. For example, as disclosed in WO 2012/086243, a liquid substance that is insoluble or hardly soluble in water is heated, and a gelling agent is added to the heated liquid substance, and the gelling agent is completely dissolved, and then the resultant sol is cooled to the sol-gel transition temperature or lower to form physical gel.

(2) Shape of Vessel of Device for Operating Magnetic Particles

The vessel 20 of the device 1 is a tubular vessel that is formed in a linear shape. As will be specifically described later, the vessel 20 is normally used in the condition that the longitudinal direction thereof is parallel with the vertical direction. The vessel 20 includes a swelling part 21, a plurality of (three) small-diameter parts 22, a plurality of (two) large-diameter parts 23, and a tip end part 24.

The swelling part 21 is disposed in the uppermost part of the vessel 20. The swelling part 21 is larger in inner diameter and outer diameter than other parts. The upper surface of the swelling part 21 has an opening, and the opening can be sealed by a cap 30 that is detachable with respect to the swelling part 21. The internal space of the swelling part 21 is one example of a sample introduction space.

The small-diameter part 22 and large-diameter part 23 are alternately disposed in the vertical direction. The small-diameter part 22 in the uppermost part is disposed below the swelling part 21. In this example, three small-diameter parts 22 are disposed at intervals in the vertical direction. The small-diameter part 22 is formed into a tubular shape that extends in the vertical direction, and extends in the equivalent shape (in a linear shape) from the upper end to the lower end. As shown in FIG. 1 and FIG. 3, a front surface 22A of the small-diameter part 22 is formed into a flat surface form along a width direction which is a direction perpendicular to the fore-and-aft direction and the vertical direction, and extends in the vertical direction. As shown in FIG. 2 and FIG. 3, a back surface 22B of the small-diameter part 22 is parallel with the width direction, and extends in the vertical direction. The back surface 22B of the small-diameter part 22 is formed into a flat surface form having a smaller dimension of the width direction than the front surface 22A, and is disposed to be parallel with the front surface 22A. By such a configuration, the small-diameter part 22 has a tapered section shape along the horizontal direction, which gradually tapers toward the back side from the front side. In the small-diameter part 22, the gel-like medium layer 12 is packed.

The large-diameter part 23 is disposed below the small-diameter part 22. In this example, below each of the two small-diameter parts 22 on the upper side, the large-diameter part 23 is disposed. That is, in this example, two large-diameter parts 23 are disposed at an interval in the vertical direction. The large-diameter part 23 is formed into a cylindrical shape extending in the vertical direction, and each of the upper end part and the lower end part thereof is tapered toward the end edge. As shown in FIG. 3, the large-diameter part 23 includes as its outer peripheral surface, a front surface 23A, a back surface 23B, a lateral surface 23C, an upper end surface 23D, and a lower end surface 23E. The front surface 23A of the large-diameter part 23 is formed into a flat surface form along the width direction, and extends in the vertical direction. The back surface 23B of the large-diameter part 23 is formed into a flat surface form along the width direction, and extends in the vertical direction. As shown in FIG. 1 and FIG. 2, the back surface 23B of the large-diameter part 23 is formed to have a larger dimension in the vertical direction than the front surface 23A, and is disposed to be parallel with the front surface 23A. The lateral surface 23C of the large-diameter part 23 (see FIG. 3) is continuous to the front surface 23A and the back surface 23B. As shown in FIG. 1, the upper end surface 23D of the large-diameter part 23 extends upward continuously from the front surface 22A and the lateral surface 23C, and is inclined inwardly (toward back side and inwardly in the width direction) as it extends upward. The lower end surface 23E of the large-diameter part 23 extends downward continuously from the front surface 22A and the lateral surface 23C, and is inclined inwardly (toward back side and inwardly in the width direction) as it extends downward. In other words, each of the upper end surface 23D and the lower end surface 23E of the large-diameter part 23 is inclined with respect to the vertical direction. The upper end surface 23D and the lower end surface 23E of the large-diameter part 23 are examples of a tapered surface.

As shown in FIG. 1 and FIG. 2, the large-diameter part 23 is disposed in the vertical direction in such a manner that it is sandwiched between the small-diameter parts 22. The outer peripheral surface of the large-diameter part 23 is continuous to the outer peripheral surface of the small-diameter part 22 disposed above the same, and the outer peripheral surface of the small-diameter part 22 disposed below the same. In particular, as shown in FIG. 2 and FIG. 3, the back surface 22B of the small-diameter part 22, and the back surface 23B of the large-diameter part 23 are continuous to each other in the condition that they are flush with each other. The sectional area (diameter) of the large-diameter part 23 is larger than the sectional area of the small-diameter part 22. Concretely, the dimension in the fore-and-aft direction of the large-diameter part 23 is larger than the dimension in the fore-and-aft direction of the small-diameter part 22, and the dimension in the width direction of the large-diameter part 23 is larger than the dimension in the width direction of the small-diameter part 22. Viewing in the vertical direction, the small-diameter part 22 is disposed on the inner side of the edge part of the large-diameter part 23. The back surface 22B of the small-diameter part 22 and the back surface 23B of the large-diameter part 23 are examples of an opposing surface.

As shown in FIG. 3, the large-diameter part 23 has a dimension in the width direction (inner diameter) L1 larger than a dimension in the fore-and-aft direction (inner diameter) L2. Concretely, the value obtained by dividing L1 in the width direction of the large-diameter part 23 by the dimension L2 in the fore-and-aft direction of the large-diameter part 23 is preferably, for example, 1.5 or more. The angle θ formed by each of the upper end surface 23D and the lower end surface 23E of the large-diameter part 23, and the vertical direction is, preferably, for example, 60° or less. In the large-diameter part 23, the liquid layer 11 (washing layer 11B) is packed.

As shown in FIG. 1 and FIG. 2, the tip end part 24 is disposed below the small-diameter part 22 in the lowermost part. The tip end part 24 is formed into a cylindrical shape extending in the vertical direction. In the tip end part 24, the liquid layer 11 (elution layer 11C) is packed. The lower end of the tip end part 24 (bottom surface of the vessel 20) is formed with an opening, and the opening is sealed with a film member 40. The target substance eluted in the eluent which is the liquid layer 11 of the tip end part 24 (elution layer 11C) can be sucked out into a pipette by inserting the pipette into the eluent in such a manner that the pipette penetrates the film member 40. The film member 40 is formed of, for example, but not limited to, aluminum. The internal spaces of the tip end part 24, the large-diameter part 23 and the small-diameter part 22 are examples of a sample migration space.

Packing of the liquid layer 11 and the gel-like medium layer 12 into the vessel 20 can be achieved by an appropriate method. When the tubular vessel 20 is used as in the present embodiment, it is preferred to seal the opening of one end (for example, lower end) of the vessel 20 prior to packing, and pack the liquid layer 11 and the gel-like medium layer 12 sequentially through the opening of the other end (for example, upper end). At this time, each of the swelling part 21, the large-diameter part 23 and the tip end part 24 is packed with the liquid layer 11. Further, the small-diameter part 22 is packed with the gel-like medium layer 12. Since the small-diameter part 22 has a small sectional area (diameter), the gel-like medium layer 12 packed in the small-diameter part 22 is stably retained in the vessel 20. Since the large-diameter part 23 has a large sectional area (diameter), the capacity of the liquid layer 11 can be made large. Therefore, it is possible to treat large quantity in the liquid layer 11.

The capacity of each part in the vessel 20, namely, the capacities of the liquid layer 11 and the gel-like medium layer 12 packed in the vessel 20 can be appropriately set depending on the amount of magnetic particles 13 to be operated, the kind of operation and so on.

In the case of providing the plurality of liquid layers 11 and gel-like medium layers 12 in the vessel 20 as in the present embodiment, the capacity of each part (each layer) may be the same or different from each other. The thickness of each part (each layer) can also be appropriately set. Considering the operability or the like, the thickness of each part (each layer) is preferably, for example, about 2 mm to 20 mm.

While the thickness of the vessel 20 is not particularly limited, when the thickness on the side of the back surface that is opposed to a permanent magnet 130 (later described) is uniform, the distance between the permanent magnet 130 and the inner peripheral surface of the vessel 20 can be kept constant, and thus the magnetic particles 13 can migrate smoothly. Therefore, the thickness of the vessel 20 is preferably uniform at least in the part packed with the gel-like medium layer 12 on the back surface side. The length of the vessel 20 is not particularly limited, and can be, for example, about 50 mm to 200 mm.

The material of the vessel 20 is not particularly limited insofar as it allows migration of the magnetic particles 13 in the vessel 20, and is capable of retaining the liquid layer 11 and the gel-like medium layer 12. In order to make the magnetic particles 13 in the vessel 20 migrate by conducting an operation of varying the magnetic field (magnetic field operation) from outside the vessel 20, a magnetic permeable material such as plastic is preferred, and examples of the magnetic permeable material include polyolefins such as polypropylene and polyethylene, fluorine resins such as tetrafluoroethylene, and resin materials such as polyvinyl chloride, polystyrene, polycarbonate, and cyclic polyolefin. As the material of the vessel 20, besides the aforementioned materials, ceramic, glass, silicone, non-magnetic metal and the like can also be used. For improving the water repellency of the inner wall surface of the vessel 20, coating with a fluorine resin or silicone may be conducted.

In the device 1, the section along the horizontal direction in the large-diameter part 23 packed with the washing layer 11B is one example of the first cross section. In FIG. 3, the first cross section is indicated by a solid line. Also in the device 1, the section along the horizontal direction in the small-diameter part 22 packed with the gel-like medium layer 12 is one example of the second cross section. In FIG. 3, the second cross section is indicated by a dotted line. As described above, the back surface 22B of the small-diameter part 22 and the back surface 23B of the large-diameter part 23 are continuous to each other while they are flush with each other. That is, the section of the large-diameter part 23 which is the first cross section, and the section of the small-diameter part 22 which is the second cross section are flush with each other in the part on the back surface side.

2. Apparatus for Operating Magnetic Particles

Figure 4:
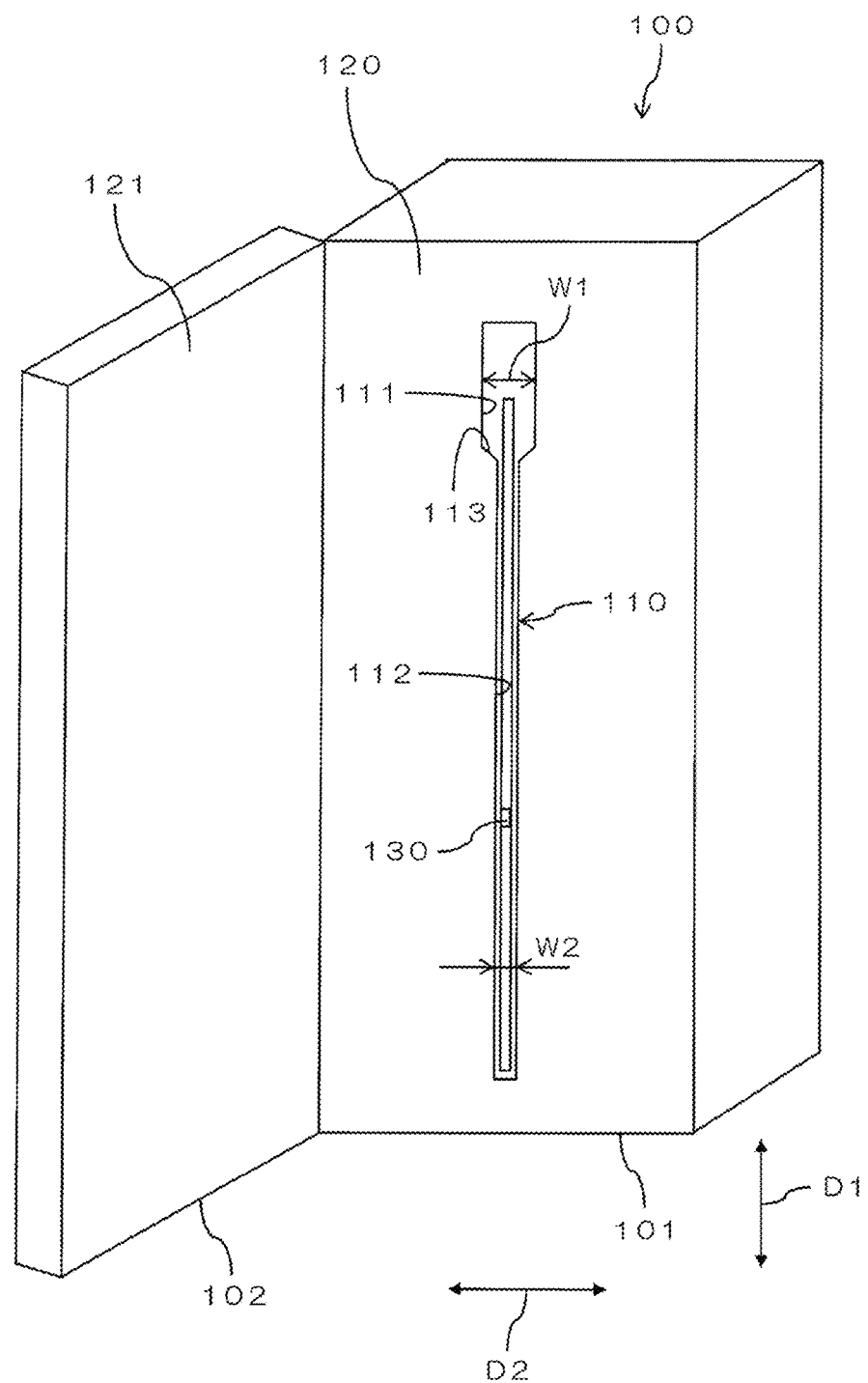
FIG. 4 is a front view showing a configuration example of an apparatus for operating magnetic particles.

FIG. 4 is a front view showing a configuration example of an apparatus for operating magnetic particles 100. The apparatus for operating magnetic particles 100 (hereinafter, referred to as "apparatus 100") is used in the condition that the device 1 shown in FIG. 1 to FIG. 3 is fixed, and is provided for conducting particle operation for a target substance contained in a liquid sample in the vessel 20 of the device 1.

The apparatus 100 includes a main body 101 formed with a vessel retaining part 110 for retaining the device 1, and a vessel pressing part 102 for pressing and fixing the vessel 20 of the device 1 retained in the vessel retaining part 110. In this example, the vessel pressing part 102 is formed by a door 121 that is rotatably attached to the main body 101 by a hinge (not illustrated). However, the vessel pressing part 102 can have a configuration capable of sliding with respect to the main body 101, or a configuration detachable with respect to the main body 101 without limited to the configuration capable of rotating with respect to the main body 101 insofar as it is configured to be able to fix the device 1 retained in the vessel retaining part 110.

The vessel retaining part 110 is formed by a recess part formed in a front surface 120 of the main body 101. In the vessel retaining part 110, a first holding part 111 for holding the swelling part 21 of the device 1, and a second holding part 112 for holding the small-diameter part 22, the large-diameter part 23 and the tip end part 24 of the device 1 are formed to extend continuously in a vertical direction D1. The vessel retaining part 110 has a width in a transverse direction D2 which is perpendicular to the direction of extension of the vessel 20 (vertical direction D1) and is parallel with the front surface 120 of the main body 101, corresponding to the device 1.

Concretely, a width W1 in the transverse direction D2 of the first holding part 111 is slightly larger than the width of the swelling part 21 of the device 1. On the other hand, a width W2 in the transverse direction D2 of the second holding part 112 is slightly larger than the width of the large-diameter part 23 of the device 1, and slightly smaller than the width of the swelling part 21. The first holding part 111 and the second holding part 112 are connected with each other by a contracting part 113 inclined with respect to the vertical direction D1. As a result, in the condition that the device 1 is held in the vessel retaining part 110, the swelling part 21 of the device 1 is caught in the contracting part 113 of the vessel retaining part 110, and retained in a suspended state.

Although not illustrated, the device 1 is held in the vessel retaining part 110 in such a manner that its longitudinal direction is parallel with the vertical direction, its front surface (the front surface 22A of the small-diameter part 22, the front surface 23A of the large-diameter part 23) faces front, and its back surface (the back surface 22B of the small-diameter part 22, the back surface 23B of the large-diameter part 23) faces back.

In this condition, the door 121 that forms the vessel pressing part 102 is closed, and thus the device 1 is fixed in the apparatus 100.

The back surface side of the vessel retaining part 110 is open, and the permanent magnet 130 is disposed so as to be opposed to the vessel retaining part 110. The permanent magnet 130 is retained slidably along the vertical direction D1. The permanent magnet 130 attracts the magnetic particles 13 in the device 1 (in the vessel 20) by magnetic force. As a result, the magnetic particles 13 are gathered on the back surface side of the vessel 20. By moving the permanent magnet 130 in the vertical direction D1 while the magnetic particles 13 are attracted to the permanent magnet 130 side in the manner as described above, it is possible to let the magnetic particles 13 in the vessel 20 migrate in the vertical direction D1.

Thus, the permanent magnet 130 constitutes a magnetic field application part for making the magnetic particles 13 in the vessel 20 migrate by varying the magnetic field. The permanent magnet 130 may be slid by a driving means such as a motor, or may be slid manually. As a magnetic force source possessed by the magnetic field application part, an electromagnet can be used in place of the permanent magnet 130. The magnetic field application part can have a plurality of magnetic force sources.

3. Operation of Magnetic Particles

Figure 5:
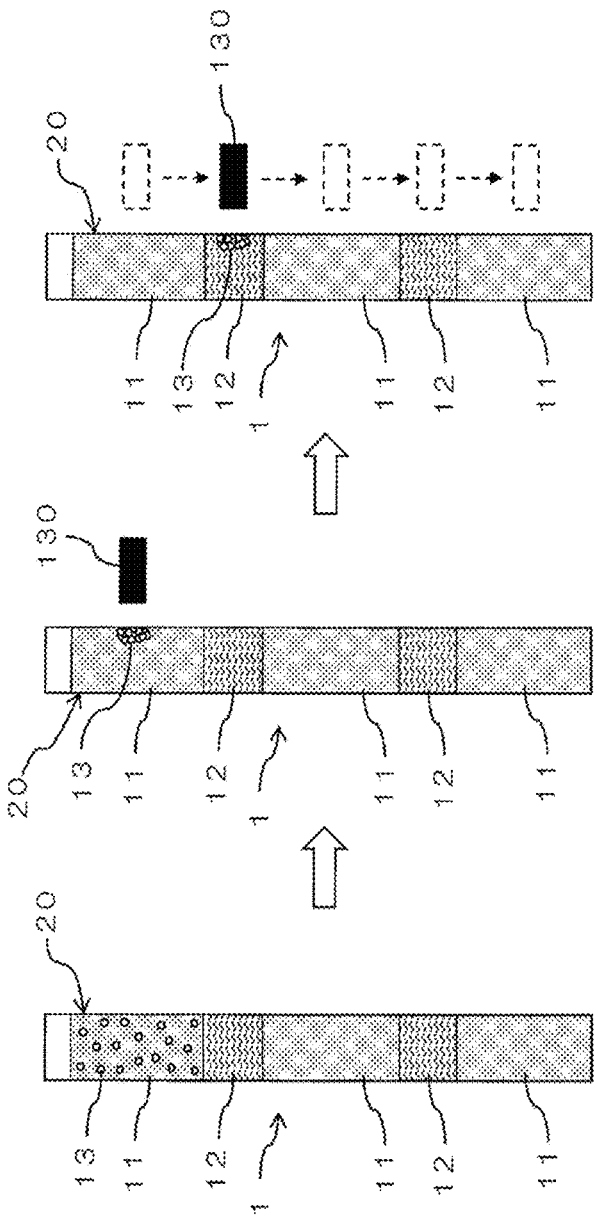
FIGS. 5A-C are schematic views for illustrating a form in operating magnetic particles.

FIGS. 5A-C are schematic views for illustrating a form in operating the magnetic particles 13. In FIGS. 5A-C, the shape of the device 1 (vessel 20) is illustrated in a simplified form for simplifying the description. In FIGS. 5A-C, the front surface side of the vessel 20 faces left, and the back surface side of the vessel 20 faces right. In FIG. 5A, in the liquid layer 11 (fixing layer 11A) in the uppermost part (swelling part 21) of the vessel 20, a liquid sample and a large number of magnetic particles 13 are contained. Although not illustrated, the liquid sample and the magnetic particles 13 are introduced into the swelling part 21 in the condition that the cap 30 of the vessel 20 (see FIG. 1) is removed. By dispersing the magnetic particles 13 in the liquid layer 11 (fixing layer 11A) in this manner, the target substance contained in the liquid layer 11 (fixing layer 11A) is selectively fixed to the magnetic particles 13.

Thereafter, as shown in FIG. 5B, the permanent magnet 130 which is a magnetic force source is brought close to the outer peripheral surface of the vessel 20 (back surface of the swelling part 21), and the magnetic particles 13 to which the target substance is fixed are gathered in the permanent magnet 130 side in the vessel 20 by the action of the magnetic field. Then, as shown in FIG. 5C, as the permanent magnet 130 is moved in the longitudinal direction of the vessel 20 (vertical direction) along the outer peripheral surface of the vessel 20, the magnetic particles 13 migrate along the longitudinal direction of the vessel 20 following the variation in the magnetic field, and sequentially migrate in the liquid layer 11 and the gel-like medium layer 12 that are stacked alternately.

Then, as the permanent magnet 130 is moved to the position opposed to the tip end part 24 (see FIG. 1), the magnetic particles 13 migrate to the liquid layer 11 (elution layer 11C) of the tip end part 24. Then, the target substance is eluted in the liquid layer 11 of the tip end part 24 (elution layer 11C).

At this time, most of the liquid physically adhered to the periphery of the magnetic particles 13 as liquid droplets come off from the surface of the magnetic particles 13 when the magnetic particles 13 enter the interior of the gel-like medium layer 12. By the entry and migration of the magnetic particles 13 into the gel-like medium layer 12, the gel-like medium layer 12 is pierced; however, the pore of the gel-like medium layer 12 is closed immediately by the self-repair action by the restoring force of the gel. Therefore, the liquid little flows into the gel-like medium layer 12 through a through-hole by the magnetic particles 13.

The magnetic particles 13 migrate along the back surface 22B of the small-diameter part 22, and the back surface 23B of the large-diameter part 23 when they migrate in the small-diameter part 22 (gel-like medium layer 12) and in the large-diameter part 23 (washing layer 11B). That is, the magnetic particles 13 migrate along a flush part in the vessel 20 when they migrate in the small-diameter part 22 (gel-like medium layer 12) and in the large-diameter part 23 (washing layer 11B). Therefore, it is possible to let the magnetic particles 13 migrate smoothly inside the vessel 20. Also as shown in FIG. 3, the back surface 22B of the small-diameter part 22 is formed to have a small dimension in the width direction. Therefore, the magnetic particles 13 migrate in the longitudinal direction of the vessel 20 in the form of a bar-like mass rather than spreading in the width direction, and pass through the gel-like medium layer 12. By letting the magnetic particles 13 migrate in the form of a bar-like mass in the longitudinal direction of the vessel 20, it is possible to make the diameter of the pore of the gel-like medium layer 12 small when the magnetic particles 13 pass. Therefore, it is possible to immediately close the pore of the gel-like medium layer 12 after passage of the magnetic particles 13, and thus, it is possible to prevent the liquid in the liquid layer 11 from mixing into other liquid layer 11.

Also, as shown in FIG. 3, the large-diameter part 23 has a large sectional area (diameter). Therefore, it is possible to increase the capacity of the liquid layer 11 (washing layer 11B), and it is possible to treat large quantity in the liquid layer 11 (washing layer 11B). Also, the large-diameter part 23 (first cross section) has a dimension in the width direction (inner diameter) L1 larger than a dimension in the fore-and-aft direction (inner diameter) L2. Therefore, it is possible to securely make the magnetic force of the permanent magnet 130 act on the magnetic particles 13 in the large-diameter part 23 while keeping the capacity of the large-diameter part 23 (washing layer 11B) large. As a result, when the permanent magnet 130 is moved in the longitudinal direction, it is possible to let the magnetic particles 13 inside the vessel 20 (inside the large-diameter part 23) migrate smoothly following the permanent magnet 130.

Also as shown in FIG. 1 and FIG. 2, in the connecting part between the small-diameter part 22 and the large-diameter part 23, the upper end surface 23D or the lower end surface 23E that is inclined with respect to the longitudinal direction is disposed (the small-diameter part 22 and the large-diameter part 23 are connected with each other by the upper end surface 23D or the lower end surface 23E that is inclined with respect to the longitudinal direction). Therefore, it is possible to prevent the magnetic particles 13 from remaining at the boundary between the small-diameter part 22 and the large-diameter part 23 when the magnetic particles 13 migrate in the vessel 20.

By dispersing the magnetic particles 13 in the liquid layer 11, and bringing the magnetic particles 13 into contact with the liquid in the liquid layer 11 in this manner, operations such as fixing of a target substance to the magnetic particles 13, a washing operation for removing impurities adhered to the surface of the magnetic particles 13, reaction of the target substance fixed to the magnetic particles 13, and elution of the target substance fixed to the magnetic particles 13 into liquid are conducted.

4. Effect of the Invention (1) According to the present embodiment, as shown in FIG. 3, the vessel 20 is formed so that the area of the first cross section that is perpendicular to the longitudinal direction of the part packed with the liquid layer 11 (large-diameter part 23) is larger than the area of the second cross section that is perpendicular to the longitudinal direction of the part packed with the gel-like medium layer 12 (small-diameter part 22).

Therefore, in the vessel 20, it is possible to reduce the diameter of the small-diameter part 22 while keeping the capacity of the large-diameter part 23 large.

As a result, in the vessel 20, it is possible to treat large quantity in the liquid layer 11 (washing layer 11B), and it is possible to retain the gel-like medium layer 12 stably.

(2) Also, according to the present embodiment, in the vessel 20, a sample introduction space which is the internal space of the swelling part 21, and a sample migration space which is the internal spaces of the small-diameter part 22, the large-diameter part 23 and the tip end part 24 are formed. In the vessel 20, in the sample migration space, the area of the first cross section that is perpendicular to the longitudinal direction of the part packed with the liquid layer 11 (large-diameter part 23) is larger than the area of the second cross section that is perpendicular to the longitudinal direction of the part packed with the gel-like medium layer 12 (small-diameter part 22).

Therefore, in the part of the vessel 20 where the sample migration space is formed, it is possible to reduce the diameter of the part packed with the gel-like medium layer 12 while keeping the capacity of the part packed with the liquid layer 11 large.

(3) According to the present embodiment, as shown in FIG. 3, in the vessel 20, the large-diameter part 23 (first cross section) is formed so that the dimension in the width direction (inner diameter) L1 is larger than the dimension in the fore-and-aft direction (inner diameter) L2.

Therefore, in the large-diameter part 23, it is possible to keep the dimension between the magnetic particles 13 in the large-diameter part 23 and the permanent magnet 130 small while keeping the capacity of the liquid layer 11 (washing layer 11B) large.

As a result, it is possible to securely make the magnetic force of the permanent magnet 130 act on the magnetic particles 13 in the large-diameter part 23.

Therefore, when the permanent magnet 130 is moved in the longitudinal direction, it is possible to let the magnetic particles 13 inside the vessel 20 (inside the large-diameter part 23) migrate smoothly following the permanent magnet 130.

(4) Further, according to the present embodiment, as shown in FIG. 3, in the vessel 20, the back surface 22B of the small-diameter part 22 and the back surface 23B of the large-diameter part 23 are continuous to each other while they are flush with each other. The magnetic particles 13 migrate along the back surface 22B of the small-diameter part 22, and the back surface 23B of the large-diameter part 23 when they migrate in the small-diameter part 22 (gel-like medium layer 12) and in the large-diameter part 23 (washing layer 11B). That is, the magnetic particles 13 migrate along a flush part in the vessel 20 when they migrate in the small-diameter part 22 (gel-like medium layer 12) and in the large-diameter part 23 (washing layer 11B).

Therefore, when the permanent magnet 130 is moved in the longitudinal direction along the vessel 20, it is possible to let the magnetic particles 13 migrate smoothly inside the vessel 20.

(5) Also according to the present embodiment, as shown in FIG. 1 and FIG. 2, in the vessel 20, in the connecting part between the small-diameter part 22 and the large-diameter part 23, the upper end surface 23D or the lower end surface 23E is disposed (the small-diameter part 22 and the large-diameter part 23 are connected with each other by the upper end surface 23D or the lower end surface 23E). The upper end surface 23D and the lower end surface 23E are inclined with respect to the longitudinal direction.

Therefore, it is possible to prevent the magnetic particles 13 from remaining at the boundary between the small-diameter part 22 and the large-diameter part 23 when the magnetic particles 13 migrate in the vessel 20.

As a result, it is possible to let the magnetic particles 13 migrate smoothly inside the vessel 20.

(6) Also, according to the present embodiment, the liquid layer 11 in the vessel 20 includes the washing layer 11B and the elution layer 11C. In the vessel 20, the capacity of the large-diameter part 23 packed with the washing layer 11B is kept large.

Therefore, in the vessel 20, a larger amount of the washing layer 11B can be packed as compared with the elution layer 11C.

5. Modified Examples of Device for Operating Magnetic Particles

Figure 6:
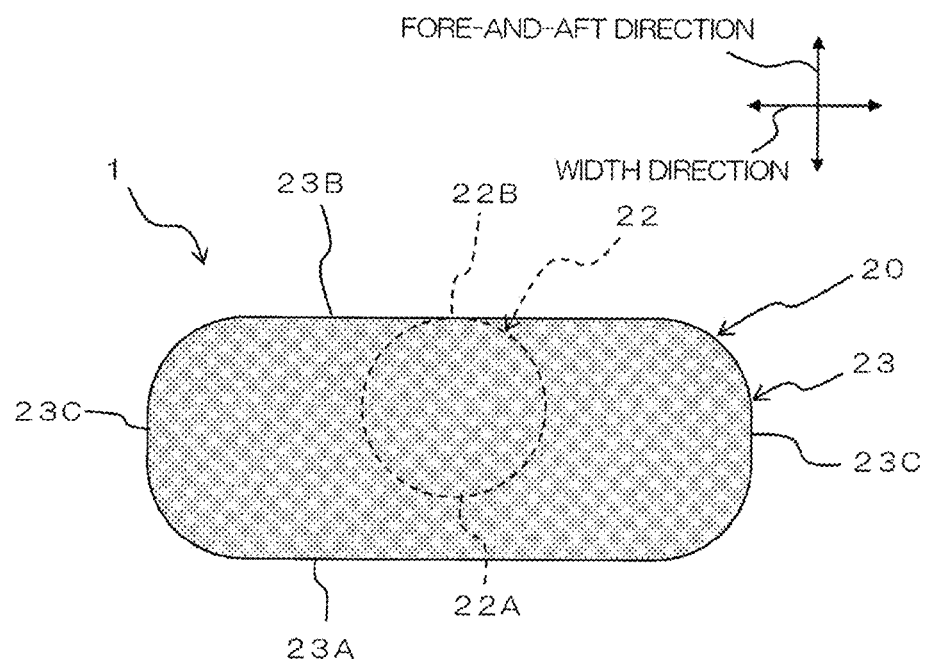
FIG. 6 is a section view showing a configuration example of a first modified example of a device for operating magnetic particles.
Figure 7:
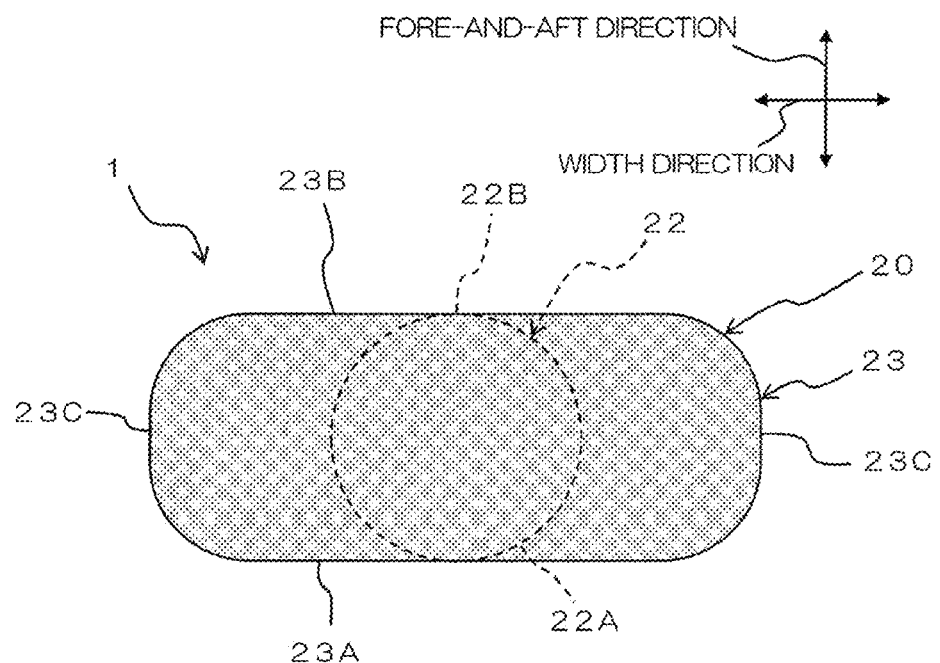
FIG. 7 is a section view showing a configuration example of a second modified example of a device for operating magnetic particles.

FIG. 6 is a section view showing a configuration example of a first modified example of a device for operating magnetic particles. FIG. 7 is a section view showing a configuration example of a second modified example of a device for operating magnetic particles.

In each of these modified examples, the section shape of the small-diameter part 22 is different from that of the configuration described above.

The example of FIG. 6 is different from the configuration of FIG. 3 in that the small-diameter part 22 is formed into a cylindrical shape extending in the vertical direction. In the configuration of FIG. 6, the dimension in the fore-and-aft direction of the large-diameter part 23 is larger than the dimension in the fore-and-aft direction of the small-diameter part 22, and the dimension in the width direction of the large-diameter part 23 is larger than the dimension in the width direction of the small-diameter part 22. Viewing in the vertical direction, the small-diameter part 22 is disposed on the inner side of the edge part of the large-diameter part 23. Also, the back surface 22B of the small-diameter part 22 and the back surface 23B of the large-diameter part 23 are continuous to each other while they are flush with each other. In FIG. 6, the part of the back surface 22B of the small-diameter part 22 is a part of the circumferential surface on the back side of the small-diameter part 22, and is a part where a contact point with a line extending in the width direction as a tangent is located. That is, the back surface 22B of the small-diameter part 22 is a part of the circumferential surface on the back side of the small-diameter part 22, and is a linear part extending in the vertical direction.

The example of FIG. 7 is different from the configuration of FIG. 3 in that the small-diameter part 22 is formed into a cylindrical shape extending in the vertical direction, and the sectional area of the small-diameter part 22 is formed to be large. In the configuration of FIG. 7, the dimension in the fore-and-aft direction of the large-diameter part 23 is almost the same with the dimension in the fore-and-aft direction of the small-diameter part 22, and the dimension in the width direction of the large-diameter part 23 is larger than the dimension in the width direction of the small-diameter part 22. Also in the configuration of FIG. 7, likewise the configuration of FIG. 6, viewing in the vertical direction, the small-diameter part 22 is disposed on the inner side of the edge part of the large-diameter part 23. Also, the back surface 22B of the small-diameter part 22 and the back surface 23B of the large-diameter part 23 are continuous to each other while they are flush with each other.

6. Other Modified Examples

In the description of the above embodiment, the washing layer 11B is packed in the large-diameter part 23, and the elution layer 11C is packed in the tip end part 24 in the vessel 20. However, in the vessel 20, each of the large-diameter part 23 and the tip end part 24 may be packed with a reaction layer for causing a predetermined reaction for a target object. In this case, in the vessel 20, it is preferred to make the shape of the tip end part 24 the same with the shape of the large-diameter part 23.

What is claimed is:

1. A device for operating magnetic particles, comprising a tubular vessel formed with an internal space where a gel-like medium layer and a liquid layer are alternately stacked in a longitudinal direction, and magnetic particles are packed, wherein
   an area of a first cross section that is perpendicular to the longitudinal direction in a part packed with the liquid layer in the internal space of the vessel is larger than an area of a second cross section that is perpendicular to the longitudinal direction in a part packed with the gel-like medium layer.

2. The device for operating magnetic particles according to claim 1, wherein
   the internal space of the vessel contains a sample introduction space and a sample migration space;
   in the sample introduction space, a sample containing a target component is introduced, said target component is fixed to the magnetic particles,
   in the sample migration space, the gel-like medium layer and the liquid layer are alternately stacked in the longitudinal direction— in the sample migration space, the target component is migrated in the longitudinal direction while fixed to the magnetic particles, the first cross section is a section perpendicular to the longitudinal direction of a part packed with the liquid layer in the sample migration space, and the second cross section is a section perpendicular to the longitudinal direction of a part packed with the gel-like medium layer in the sample migration space.

3. The device for operating magnetic particles according to claim 1, wherein in the vessel, a magnetic field application part on one longitudinal surface of the vessel is movable along the longitudinal direction; wherein said one longitudinal surface is opposite an opposing surface; and in the first cross section, an inner diameter of the opposing surface is larger than an inner diameter in a direction perpendicular to the opposing surface.

4. The device for operating magnetic particles according to claim 3, wherein a part opposed to the magnetic field application part on the opposing surface side in the first cross section and a part opposed to the magnetic field application part on the opposing surface side in the second cross section are aligned with each other in the longitudinal direction.

5. The device for operating magnetic particles according to claim 1, wherein the part packed with the liquid layer and the part packed with the gel-like medium layer in the internal space of the vessel are connected with each other by a tapered surface inclined with respect to the longitudinal direction.

6. The device for operating magnetic particles according to claim 1, wherein the liquid layer includes a washing layer packed with a washing liquid for washing a target substance in a sample, and an elution layer packed with an eluent for eluting a target component in the sample, and the first cross section is a section perpendicular to the longitudinal direction of the washing layer in the internal space of the vessel.

* * * * *